United States Patent [19]
Ryu et al.

[11] Patent Number: 6,021,346
[45] Date of Patent: Feb. 1, 2000

[54] METHOD FOR DETERMINING POSITIVE AND NEGATIVE EMOTIONAL STATES BY ELECTROENCEPHALOGRAM (EEG)

[75] Inventors: Chang Su Ryu; Seon Hee Park; Seung Hwan Kim, all of Daejeon, Rep. of Korea

[73] Assignee: Electronics and Telecommunications Research Institute, Daejeon, Rep. of Korea

[21] Appl. No.: 09/121,353

[22] Filed: Jul. 23, 1998

[30] Foreign Application Priority Data

Nov. 13, 1997 [KR] Rep. of Korea ............... 97-59872

[51] Int. Cl.[7] .................................................. A61B 5/04
[52] U.S. Cl. ........................................ 600/544; 600/300
[58] Field of Search .................................. 600/544, 545, 600/300, 301

[56] References Cited

U.S. PATENT DOCUMENTS

| | | | |
|---|---|---|---|
| 5,010,891 | 4/1991 | Chamoun | 600/544 |
| 5,083,571 | 1/1992 | Prichep | 600/544 |
| 5,601,090 | 2/1997 | Musha | 600/544 |

OTHER PUBLICATIONS

Tzyy–Ping Jung, Scott Makeig, Magnus Stensmo and Terrance J. Sejnowski, "Estimating Alterness from the EEG Power Spectrum", JEEE Transactions on Biomedical Engineering, Jan., 1997, pp. 60–69.

*Primary Examiner*—Max Hindenburg
*Assistant Examiner*—Navin Natnithithadha
*Attorney, Agent, or Firm*—Cohen, Pontani, Lieberman & Pavane

[57] ABSTRACT

The present invention to provide a method for determining positive and negative emotional states by using a relative power in a subband of a specific frequency band increases or decreases in the course of time. In order to realize the above object, the present invention determines positive and negative emotional states by using a relative power in a subband of a specific frequency band increases or decreases with the lapse of time. The present invention performs a Fourier transform for a unit time not an entire response time regarding a stimulus, and can be used in real time by using a time-frequency analysis method continuously executed with the lapse of time.

4 Claims, 3 Drawing Sheets

METHOD FOR DETERMINING POSITIVE AND NEGATIVE EMOTIONAL STATES BY ELECTROENCEPHALOGRAM (EEG)

BACKGROUND OF THE INVENTION

1. Field of the Invention

The present invention relates generally to a method for determining positive and negative emotional states by electroencephalogram (hereinafter referred to as an EEG). More particularly, it relates to a method for determining positive and negative emotional states by using that a relative power in a subband of a specific frequency band increases or decreases with the lapse of time.

2. Description of the Prior Art

In recent years, for a human being comfortable life, the information about a human being emotional state as a response to a peripheral environment has been requested to a product development research. Accordingly, a technique for estimating a human being response (i.e., emotional state) for the peripheral environment is required thereto.

To achieve the above technique, an EEG analysis method has been developed. The EEG analysis method discriminates between a pleasant emotion and a bad (unpleasant) emotion of human by using the EEG, which is applied to both a human's taste research and a product development.

There are two kinds of methods for analyzing the EEG, i.e., a linear analysis method such as a Fourier transform and a nonlinear analysis method such as a correlation dimension estimation.

The Fourier transform can obtain the information for a specific frequency component such as α-wave (8–13 Hz) and β-wave (14–30 Hz) extensively studied. The correlation dimension estimation is used to determine whether or not EEG time series are chaos signals.

Since a conventional EEG analysis method uses all data of a response usually time (30 seconds–1 minute) for a stimulus, it is difficult to perform a real-time processing.

Also, the conventional EEG analysis method cannot be applied to a nonstationary EEG having a large variation in the course of time. Since the conventional EEG analysis method needs a reference line for comparing a present state with another state, it should measure EEG generated when no stimulus is applied to the human.

The conventional method for determining positive and negative emotional states can enhance an accuracy of a discrimination by analyzing a physiological signal (such as an electrocardiogram (ECG), a peripheral blood pressure, a galvanic skin resistance and a person's face expression) as well as the EEG. However, the user feels inconvenient in using the conventional method as a man-machine interface.

SUMMARY OF THE INVENTION

The present invention is directed to a method for determining positive and negative emotional states by EEG which substantially obviates the above-described problem due to limitations and disadvantages of the related art.

It is an object of the present invention to provide a method for determining positive and negative emotional states by using a relative power in a subband of a specific frequency band increases or decreases in the course of time.

In order to realize the above object, the present invention determines positive and negative emotional states by using a relative power in a subband of a specific frequency band increases or decreases with the lapse of time. The present invention performs a Fourier transform for a unit time not an entire response time regarding a stimulus, and can be used in real time by using a time-frequency analysis method continuously executed with the lapse of time. The present invention determines positive and negative emotional states by using only that the relative power in a subband of a specific frequency band increases or decreases with the lapse of time, and does not need a reference line. In addition, the present invention analyzes only EEG measured by a few electrodes on the scalp, thereby minimizing the user's inconvenience when it is employed as a man-machine interface.

A method for determining positive and negative emotional states by EEG includes:

a first step for performing a fast Fourier transform of EEG which is measured by one electrode attached on the scalp during a specific unit time;

a second step for dividing a specific frequency band of Fourier-transformed values into subbands, and calculating a relative power in a subband;

a third step for repeating the first and second steps, and calculating a relative power against time in the subbands;

a fourth step for performing a smoothing operation to take an average value over the relative power obtained from the third step and nearest neighbors, and thus ignoring a fluctuation within a short time;

a fifth step for calculating an increasing/decreasing slope in time by using a least square-fit for a smoothed data of the fourth step;

a sixth step which introduces threshold value into the increasing/decreasing slope calculated in the fifth step, and determines an increase or a decrease in time with reference to the threshold over the increasing/decreasing slope calculated in the fifth step; and a seventh step which determines an emotional state as a negative emotional state if a relative power in a low-frequency band decreases and a relative power in a high-frequency band increases, and determines an emotional state as a positive emotional state if a low-frequency component increases and a high-frequency component decreases.

Additional features and advantages of the invention will be set forth in the description which follows, and in part will be apparent from the description, or may be learned by practice of the invention. The objective and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENT

Reference will now be made in detail to the preferred embodiment of the present invention, examples of which are illustrated in the accompanying drawings.

Figure 1:
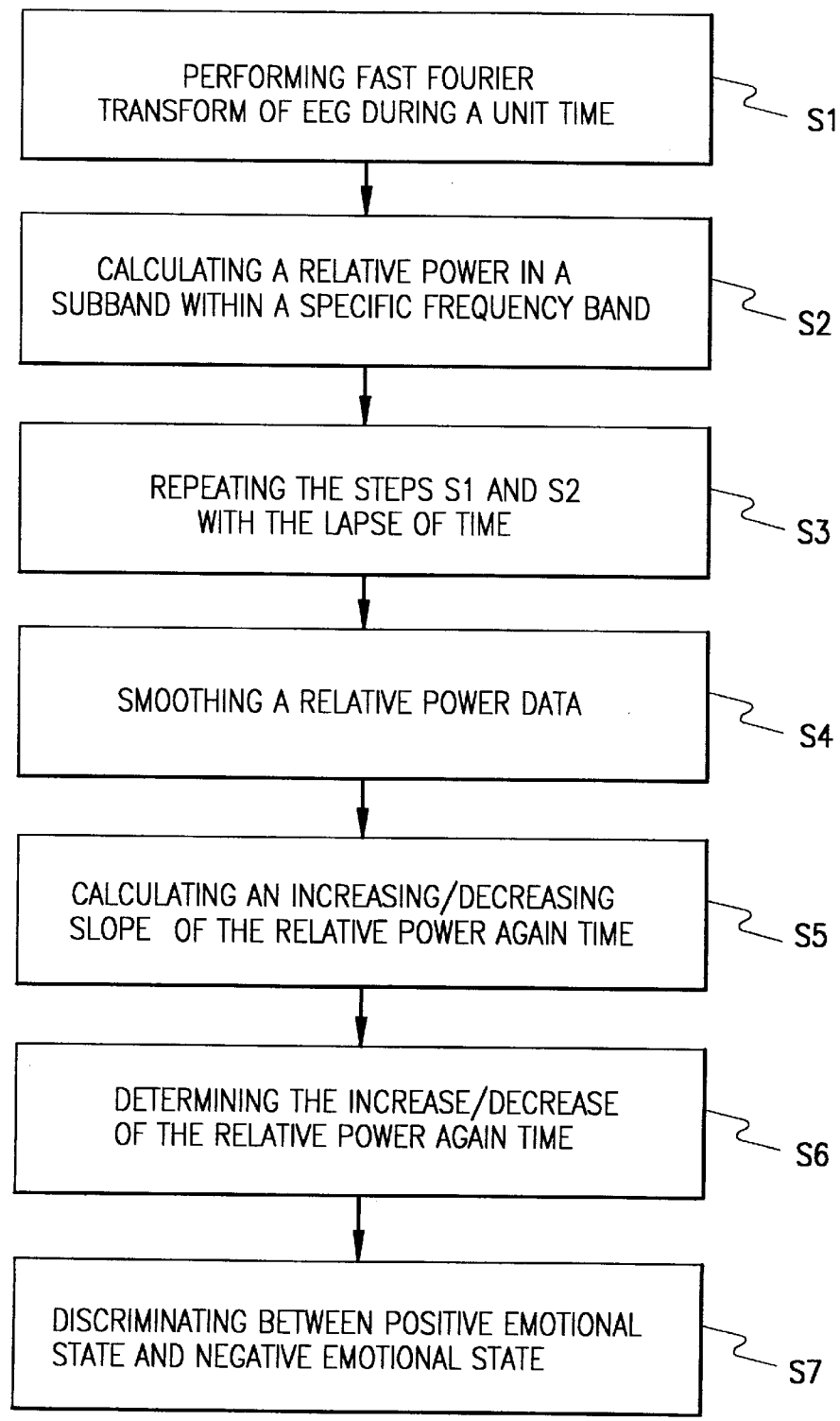
FIG. 1 is a flowchart illustrating a method for analyzing EEG in accordance with a preferred embodiment of the present invention.

FIG. 1 is a flowchart illustrating a method for analyzing EEG in accordance with a preferred embodiment of the present invention, and includes the following 7 steps.

A fast Fourier transform of EEG measured by one electrode attached on a human scalp for a specific unit time is performed in the step S1. Herein, the electrode is set to F4 or F3 on the scalp in 10–20 international electrode placement system.

A step S2 selects α-wave (8–13 Hz) as a specific frequency band, herein, the α-wave (8–13 Hz) is insensitive to artifacts such as an eye blink, an eye movement, and an electromyogram (EMG).

Then, the step S2 divides the specific frequency band into subbands such as A(8–9 Hz), B(9–10 Hz), C(10–11 Hz), and D(11–13 Hz), obtains spectral powers $P_A$, $P_B$, $P_C$ and $P_D$, divides the spectral powers $P_A$, $P_B$, $P_C$ and $P_D$ by an total power $P_A+P_B+P_C+P_D$ of α-wave band, thereby calculating a relative power. Herein, the reason for calculating the relative power is to prevent that a variation of a frequency component appears as if the variation was present in the specific frequency band due to an amplification of EEG within all frequency bands, even if there is no variation of the frequency component in the specific frequency band. The present invention can be applied to a case that the subband is differently set or to other case that a specific frequency band excepting the α-wave band is selected.

A step S3 continuously repeats the steps S1 and S2 with the lapse of time, obtains a relative power against the time with respect to the subbands A, B, C and D.

A step S4 performs a smoothing operation to taking an average value over the relative power and nearest neighbor data, in order to ignore a fluctuation within a short time with reference to the relative power obtained from the step S3.

A step S5 obtains an increasing/decreasing slope with the lapse of time by using a least square-fit for the smoothed data in the step S4. Here, a time unit used to obtain the increasing/decreasing slope should be determined in consideration of both an accuracy and a speediness of a discrimination.

A step S6 employs a threshold value proper to the increasing/decreasing slope obtained from the step S5, and determines an increase or a decrease with the lapse of time with reference to the threshold slope of the increasing/decreasing slope.

A step S7 determines an emotional state as a negative emotional state (i.e., unpleasant emotional state) if a low frequency component (i.e., a slow α-wave) decreases and a high frequency component (i.e, a fast α-wave) increases in the step S6, and determines an emotional state as a positive emotional state (i.e., pleasant emotional state) if the low frequency component increases and the high frequency component decreases in the step S6.

Figure 2:
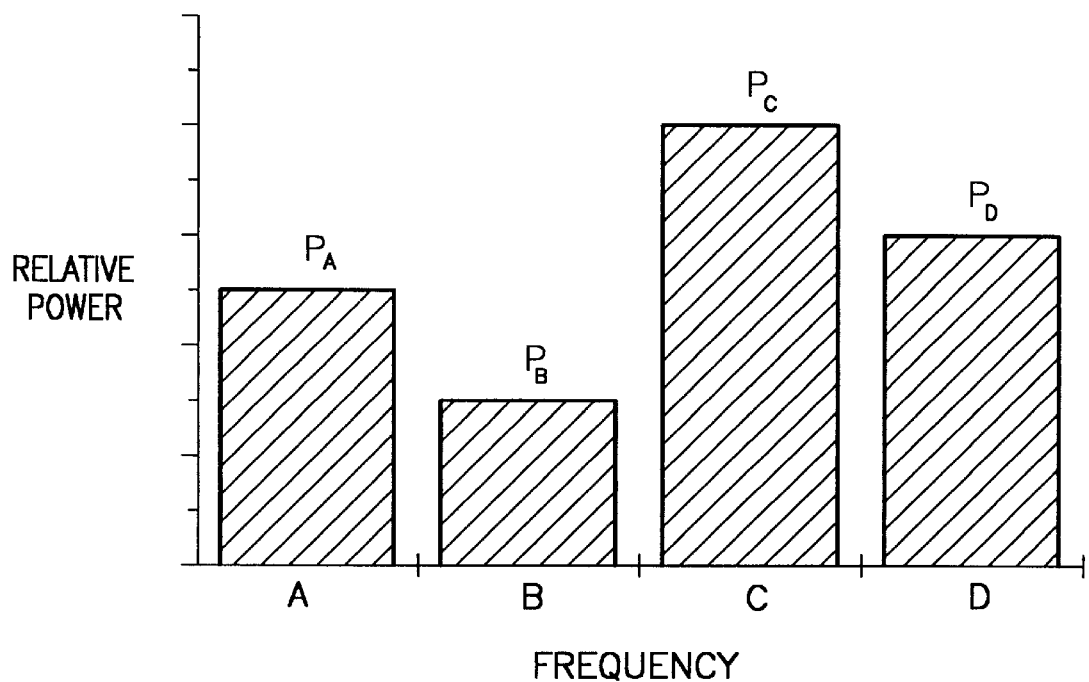
FIG. 2 is an output graph during a unit time for a subband of a specific frequency band in accordance with a preferred embodiment of the present invention.

FIG. 2 is an output graph during a unit time about subbands of a specific frequency band in accordance with a preferred embodiment of the present invention. More specifically, FIG. 2 depicts the output data $P_A$, $P_B$, $P_C$ and $P_D$ with reference to the subbands A(8–9 Hz), B(9–10 Hz), C(10–11 Hz) and D(11–13 Hz).

Figure 3:
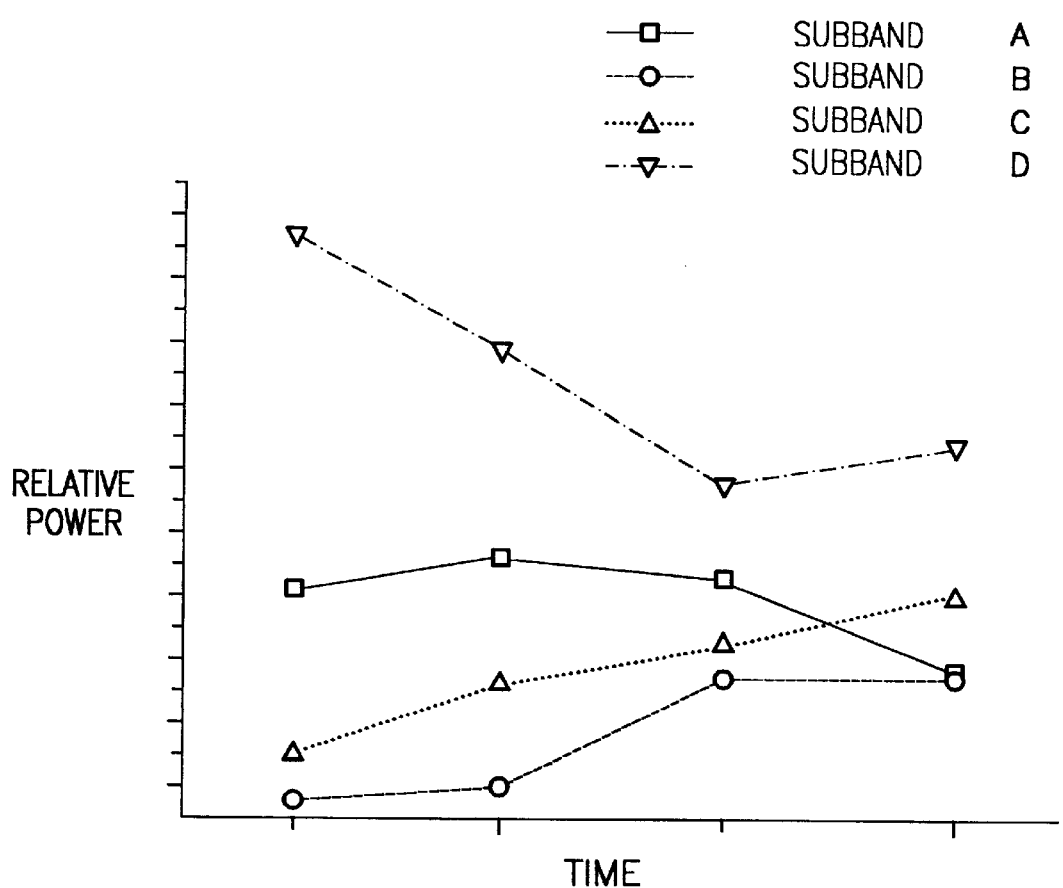
FIG. 3 is a graph showing that a relative power in the frequency subband of FIG. 2 increases or decreases with the lapse of time.

FIG. 3 is a graph showing an EEG variation generated by that relative powers in the frequency band of FIG. 2 increase or decrease with the lapse of time. More specifically, FIG. 3 shows that a relative power obtained by dividing each of the output data $P_A$, $P_B$, $P_C$ and $P_D$ by the entire output data $P_A+P_B+P_C+P_D$ of α-wave band, changes with the lapse of time.

As described above, the present invention determines positive and negative emotional states by that a relative power in subbands of a specific frequency band increases or decreases with the lapse of time. The present invention performs a Fourier transform for a unit time not an entire response time to a stimulus, and can be used in a real-time processing by using a time-frequency analysis method continuously executed with the lapse of time. The present invention determines positive and negative emotional states by using only that the relative power in a subband of a specific frequency band increases or decreases with the lapse of time, so that a reference line is not needed to the present invention. In addition, the present invention analyzes only EEG measured on a few electrodes without using other physiological signal or a human face expression, thereby minimizing the user's inconvenience when it is employed as a man-machine interface.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

What is claimed is:

1. A method for determining positive and negative emotional states of a subject with an electroencephalogram (EEG) which uses a Fourier transform, comprising the steps of:

a. performing a fast Fourier transform on an EEG signal measured by an electrode attached to a scalp of the subject during a specific unit of time;

b. dividing a specific frequency band of the Fourier-transformed EEG signal from step a. into subbands and calculating a relative power;

c. repeating steps a. and b. and calculating the relative power relative to time in the subbands;

d. performing a smoothing operation for obtaining an average value of the relative power measured in step c. and neighboring data, thereby ignoring fluctuations within short periods of time;

e. calculating a slope as a function of time using a least square fit for the smoothed data of step d.;

f. introducing a threshold value into the slope calculated in step e. and determining an increase or decrease against time in response to the threshold value of the slope calculated in step e.;

g. determining an emotional state as a negative emotional state if a low frequency component having the slope in step e. decreases during step f. or if a high frequency component having the slope in step e. increases during step f.; and h. determining an emotional state as a positive emotional state when the low frequency component increases in step f. or the high frequency component decreases in step f.

2. The method of claim 1, wherein said step a. comprises setting a position of the electrode to one of F4 or F3 in the 10–20 international electrode placement system.

3. The method of claim 1, wherein said step b. comprises selecting an α-wave (8–13 Hz) as the specific frequency band, the α-wave being insensitive to artifacts including an eye blink, eye movement, and an electromyogram (EMG).

4. The method of claim 3, wherein said step b. comprises dividing the specific frequency band into subbands A (8–9 Hz), B (9–10 Hz), C (10–11 Hz), and D (11–12 Hz), obtaining spectral powers $P_A$, $P_B$, $P_C$, and $P_D$ from respective subbands A, B, C, and D and dividing the spectral powers $P_A$, $P_B$, $P_C$, and $P_D$ by a total power $P_A+P_B+P_C+P_D$ of the specific frequency band for calculating the relative power.

* * * * *